United States Patent [19]

Patel et al.

[11] Patent Number: 5,348,736
[45] Date of Patent: Sep. 20, 1994

[54] STABILIZED HAIR-TREATING COMPOSITIONS

[75] Inventors: Amrit M. Patel, Dayton; Clarence R. Robbins, Martinsville, both of N.J.

[73] Assignee: Colgate-Palmolive Company, New York, N.Y.

[21] Appl. No.: 568,283

[22] Filed: Aug. 16, 1990

Related U.S. Application Data

[63] Continuation-in-part of Ser. No. 507,328, Apr. 9, 1990, Pat. No. 4,997,641, which is a continuation-in-part of Ser. No. 507,335, Apr. 9, 1990, Pat. No. 5,213,716, which is a continuation-in-part of Ser. No. 369,361, Jun. 21, 1989, abandoned, which is a continuation-in-part of Ser. No. 369,389, Jun. 21, 1989, abandoned, which is a continuation-in-part of Ser. No. 432,644, Nov. 7, 1989, Pat. No. 5,051,250, which is a continuation-in-part of Ser. No. 432,952, Nov. 7, 1989, abandoned.

[51] Int. Cl.$^5$ ............................................. A61K 7/075
[52] U.S. Cl. .................... 424/70; 252/89.1; 252/106; 252/550; 252/551; 252/DIG. 5; 252/DIG. 13; 252/DIG. 14; 424/47; 424/71; 514/772; 514/789; 514/852; 514/880; 514/881; 514/944
[58] Field of Search ............ 424/47, 70, 71; 252/DIG. 13, DIG. 14, DIG. 5, 106, 89.1, 550, 551; 514/772, 789, 852, 880, 881, 944; A61K 7/075, 7/08, 7/50, 7/11

[56] References Cited

U.S. PATENT DOCUMENTS

| | | | |
|---|---|---|---|
| 2,891,912 | 6/1959 | Schwartz | 252/152 |
| 2,950,254 | 8/1960 | Meinhard et al. | 252/152 |
| 3,950,510 | 4/1976 | Adams | 252/DIG. 13 X |
| 3,969,500 | 7/1976 | Kennerly | 424/10 |
| 4,000,077 | 12/1976 | Wixon | 252/8.75 |
| 4,078,147 | 3/1978 | Ukai et al. | 424/70 X |
| 4,470,982 | 9/1984 | Winkler | 424/245 |
| 4,486,334 | 12/1984 | Horiuchi et al. | 252/312 |
| 4,544,498 | 10/1985 | Suzuki et al. | 252/547 |
| 4,563,347 | 1/1986 | Starch | 424/70 |
| 4,654,163 | 3/1987 | Quack et al. | 252/312 |
| 4,654,207 | 3/1987 | Preston | 424/70 |
| 4,701,322 | 10/1987 | Dixon et al. | 424/70 |

(List continued on next page.)

FOREIGN PATENT DOCUMENTS

| | | | |
|---|---|---|---|
| 0413417 | 2/1991 | European Pat. Off. | A61K 7/08 |
| 8806434 | 9/1988 | PCT Int'l Appl. | A61K 7/06 |

OTHER PUBLICATIONS

Patent Abstracts of Japan, vol. 10, No. 63, "Treatment of Skin", Shiseido, 60-202813, Oct. 14, 1985.
Patent Abstracts of Japan, vol. 11, No. 43, "Hair Tonic", Asama, 61-207321, Sep. 13, 1986.
Patent Abstracts of Japan, vol. 14, No. 265, "Pack Agent for Make-Up", Nippon Oil & Fats Co. Ltd., 2-78605, Mar. 19, 1990.
Tied et al., *Chemistry and Industry*, Oct. 27, 1951, pp. 911–912.
Archer Daniels Midland Bulletin No. 907-R, p. 10.
Petrolite Brochure—Unilin alcohols—SP-1040 1985.

*Primary Examiner*—Thurman K. Page
*Assistant Examiner*—Robert H. Harrison
*Attorney, Agent, or Firm*—Robert C. Sullivan; Richard J. Ancel

[57] ABSTRACT

Liquid fiber-treating and skin-treating compositions include surfactant, water insoluble treating material, water and long chain alcohol or derivative thereof, which stabilizes the liquid so as to allow storage at elevated temperatures, such as those which can be reached during storage in warmer climates, and which also helps to make fiber- and skin-treating materials more substantive to fibers and skin. Among the various types of compositions benefited are shampoos, perfuming shampoos, hair conditioning compositions, hair setting compositions, anti-dandruff preparations, fabric softening compositions, antistatic compositions, detergents, skin cleansers, skin lotions and sunscreens.

12 Claims, No Drawings

U.S. PATENT DOCUMENTS

| | | | |
|---|---|---|---|
| 4,704,272 | 11/1987 | Oh et al. | 424/70 |
| 4,707,293 | 11/1987 | Ferro | 252/174.17 |
| 4,711,776 | 12/1987 | Suzuki et al. | 424/70 |
| 4,717,501 | 1/1988 | Hirota et al. | 252/311 |
| 4,726,944 | 2/1988 | Osipow et al. | 424/70 |
| 4,728,457 | 3/1988 | Fieler et al. | 252/174.15 |
| 4,741,855 | 5/1988 | Grote et al. | 252/142 |
| 4,765,975 | 8/1988 | Iovanni et al. | 424/70 |
| 4,772,427 | 9/1988 | Dawson et al. | 252/DIG. 13 |
| 4,772,462 | 9/1988 | Boothe et al. | 424/70 |
| 4,777,038 | 10/1988 | Scheuffgen | 424/70 |
| 4,777,039 | 10/1988 | Lang et al. | 424/70 |
| 4,803,237 | 2/1989 | Light | 524/385 |
| 4,824,602 | 4/1989 | Juneja | 252/547 |
| 4,830,774 | 5/1989 | LaPetina et al. | 424/70 X |
| 4,855,130 | 8/1989 | Konrad | 424/70 |
| 4,859,550 | 8/1989 | Gruber et al. | 430/39 |
| 4,859,732 | 8/1989 | Minnick et al. | 525/385 |
| 4,867,971 | 9/1989 | Ryan et al. | 424/70 X |
| 4,933,176 | 6/1990 | Van Reeth | 424/70 |
| 5,034,218 | 7/1991 | Duvel | 424/70 |
| 5,096,697 | 3/1992 | Adachi et al. | 424/70 X |

STABILIZED HAIR-TREATING COMPOSITIONS

This is a continuation-in-part of application Ser. No. 07/507,328, filed Apr. 9, 1990, U.S. Pat. No. 4,997,641, which is a continuation-in-part of application Ser. No. 07/507,335, filed Apr. 9, 1990, U.S. Pat. No. 5,213,716, which is a continuation-in-part of application Ser. No. 07/369,361, filed Jun. 21, 1989, abandoned, which is a continuation-in-part of application Ser. No. 07/369,389, filed Jun. 21, 1989, abandoned, which is a continuation-in-part of application Ser. No. 07/432,644, filed Nov. 7, 1989, U.S. Pat. No. 5,051,250, which is a continuation-in-part of application Ser. No. 07/432,952, filed Nov. 7, 1989, abandoned.

This invention relates to compositions of types which are used for treating fibrous materials and/or human skin. More particularly, it relates to liquid compositions of improved stabilities which include a fiber- or skin-treating material which is insoluble-or poorly soluble in a liquid medium, which compositions are of improved stabilities at elevated temperatures, due to the presence in their formulas of a long chain alcohol or a derivative thereof.

Liquid state fiber-treating and skin-treating compositions of various types have long been known and stability problems with such compositions have often been experienced, evidenced by precipitation or separation out from the continuous medium thereof of components, such as water insoluble active fiber- and skin-treating agents, and other suspended, dispersed or emulsified components, which are often strongly lipophilic and hydrophobic. Among fiber treating compositions there may be mentioned hair-treating compositions, including shampoos, hair perfuming shampoos, hair conditioning shampoos, anti-dandruff shampoos, hair dyeing compositions, including hair coloring shampoos, and anti-dandruff preparations, fabric softening compositions, anti-static compositions, and detergents, and among the skin-treating compositions are skin cleansers, skin lotions and sunscreens.

Cetyl and stearyl alcohols have been suggested for uses in various cosmetics, including skin lotions. They have also been suggested for inclusion in shampoos. However, applicants do not believe that before the present invention and before the inventions described in the previously mentioned parent applications, their invention, of the employment of certain higher fatty alcohols or derivatives thereof as stabilizing agents in the described types of compositions, was known. Although higher fatty alcohols and derivatives thereof, such as esters, had been included in shampoos, liquid detergents and skin care products, high molecular weight or long chain alcohols and their derivatives, of types used in the present invention, had not been incorporated in such fiber-treating and skin-treating products with water insoluble or relatively water insoluble fiber- or skin-treating components, which were often desired to be substantive to the fiber or skin after normal use of the composition, and the desirable stabilizing and substantivity enhancing properties of the long chain alcohols and derivatives had not been noted. Accordingly, it is considered that this invention is novel and unobvious, and therefore it is patentable.

In accordance with the present invention a liquid fiber- or skin-treating composition of improved elevated temperature stability, due to its content of a stabilizing agent which is a long chain alcohol or suitable derivative thereof, comprises a liquid medium for the composition, an emulsifying agent, a fiber- or skin-treating material which is insoluble in the liquid medium but is suspended or dispersed in such medium, and such a long chain alcohol or derivative thereof which is of a weighted average chain of 26 to 43 carbon atoms.

In a search for prior art the following U.S. patents were noted, which may be of some relevance to this invention:

| | | |
|---|---|---|
| 3,969,500; | 4,707,293; | 4,824,602; |
| 4,470,982; | 4,726,944; | 4,850,732; |
| 4,701,322; | 4,729,457; | 4,885,130 and |
| 4,704,272; | 4,803,237; | 4,859,500 |

Also of interest is the Petrolite Corporation bulletin entitled UNILIN TM Alcohols, copyrighted in 1985 and identified as SP-1040. That bulletin mentions various possible applications for the UNILIN alcohols described therein (which are mixtures of a major proportion of saturated primary linear polymeric alcohols of about 28 to 48 carbon atoms, on the average, with a minor proportion of saturated hydrocarbons of equivalent carbon atom contents), including uses as specialty chemical intermediates and as functional polymers. The bulletin teaches that as functional polymers the UNILIN alcohols are of improved compatibility with solvents and other polymers and that under high temperature conditions the alcohols or their derivatives "can be used for improved performance without product degradation". Applications of the UNILIN alcohols as functional polymers mentioned in the bulletin include uses in coatings, plastic additives and specialty nonionics. The bulletin also states that the hydrophobic/hydrophilic balance of such alcohol molecule allows for higher levels of water-insoluble material to be incorporated into an aqueous system, co-emulsificiation takes place easily with a wide variety of anionic and nonionic emulsifiers and a more water-insoluble film-can be formed with UNILIN alcohols as part of the emulsifier system. However, there is no disclosure in the patents or in the bulletin that the UNILIN alcohols will improve the long term storage stability at elevated temperature of fiber-treating and skin-treating compositions, such as shampoos and sunscreen lotions, and the bulletin does not teach that water-insoluble materials, such as hair conditioning and skin conditioning compounds, will be made more substantive to the substrates to which they are applied from their respective compositions. (and thus will be more effective conditioning agents). Furthermore, the reference does not indicate that the UNILIN alcohols will have a desirable pearlescing effect when incorporated in many of the liquid fiber-treating or skin-treating compositions of this invention.

In a broad aspect of this invention the conditioning compositions thereof may be in liquid, creme, gel or paste form. Although stabilization thereof is of prime significance for only the liquid compositions, compositions in the other physical forms are also of improved substantivity of active components and all such compositions may be made desirably pearlescing by their contents of the long chain alcohols.

The long chain primary alcohol of the present compositions may be saturated or unsaturated but are preferably saturated. Also the single hydroxyl may be located in a terminal carbon of a short alkyl branch off a main carbon chain but preferably the alcohol is unbranched. Similarly, hydrogens of the chain may be substituted by other relatively inactive atoms and groups, such as halogens and etheric groups but preferably the carbons of the alcohol chain will be unsubstituted. The long chain primary alcohol will normally be a mixture of homologous alcohols, all of which are often of even numbers of carbon atoms, usually being in the range of 18 to 54 carbon atoms, averaging (on a weight or weighted basis) in the range of 26 to 43 carbon atoms and very preferably normally averaging 29 or 30 to 38, 39 or 40 carbon atoms. Such mixtures will be of normal or substantially normal distribution curves. Preferably the average carbon content will be in the range of 28 to 42 carbon atoms per mole and preferred alcohol mixes will average 30 to 40 carbon atoms or about such numbers. When the average number of carbon atoms in the chain is less than 26 the stabilizing and adherence promoting effectivenesses of such alcohols in the present formulations is less than desired, with the stabilizing, conditioning and pearlescing actions, or some of them, being diminished, and when the chain length is more than an average of 43 atoms dispersibility of the alcohols and stability of the insoluble agents in the described compositions is often unsatisfactory.

With the long chain alcohols of the UNILIN alcohols there will be present corresponding saturated hydrocarbons, which are also of even numbers of carbon atoms. However, whereas the distribution curve of the alcohols is normal or substantially normal, that of the hydrocarbons is substantially flat, with the content of any one hydrocarbon normally being within the range of 0.5 to 3% or about 1 to 2% of the total of all the alcohols and hydrocarbons, and with the total of hydrocarbons contents normally being less than ⅓ of such alcohols contents (less than ¼ of the total alcohol plus hydrocarbon content). Preferably the hydrocarbon content is less than ¼ of the alcohol content (less than 1/5 of the total). The alcohols (and corresponding hydrocarbons) present will normally be of chain lengths such that at least 80% are in the range of 18 to 54 carbon atoms, with at least 80% being in the range of 18 to 44 carbon atoms for an alcohol averaging about 30 carbon atoms and with at least 80% being in the range of about 28 to 54 carbon atoms when the alcohol averages about 40 carbon atoms. The normal distribution curve mentioned above is substantially bell-shaped and somewhat flattened at its upper part so that the content of any one alcohol does not exceed 10% of the UNILIN (including hydrocarbon content). In addition to the mentioned long chain alcohols, related compounds such as corresponding alkoxylated alcohols, corresponding fatty acids and long chain saturated primary lower ($C_{1-4}$) alcohol esters, may be substituted, at least in part. Of such "derivatives" the alkoxylated alcohols are preferred, and the most preferred of these are the ethoxylated alcohols, which will normally contain up to about 20 ethoxy groups per mole, e.g., about 10 to 20. However, the alcohols, which are the preferred embodiments of the invention, will desirably be employed alone or in mixture with related compounds from the "derivatives" group, with the alcohols being the major proportion of the total "alcohol plus derivatives" content.

Preferred UNILIN's are UNILIN's 425 and 550, wherein the weighted average carbon atoms contents of the alcohols (and the hydrocarbons) are about 30 and 40, respectively. UNILIN's 325 and 350, which are of lower molecular weights, may also be useful especially when employed in mixture with UNILIN's 425 and/or 550. Distributions of the alcohol and hydrocarbon components for UNILIN 425 are shown in a bar graph(connecting of the tops of which makes a distribution curve) in the mentioned Petrolite bulletin, which is hereby incorporated herein by reference. Similar distribution curves, displaced sidewardly because of different numbers of carbon atoms in the products, are considered to be descriptive of the other UNILIN's which are useful in the practice of this invention.

While it is preferred to utilize the UNILIN's it is within this invention to employ individual alcohols of chain lengths averaging (and preferably being) within the $C_{26-43}$ range, and such alcohols may be employed with or without similar proportions of hydrocarbons, as in the UNILIN's. Similarly, such may be employed with derivatives of the UNILIN's, such as UNITHOX TM 550, which is an ethoxylated derivative of UNILIN 550, or such derivatives may be employed alone as the stabilizing agent.

Because it is awkward to have to recite long chain alcohol and derivatives thereof repeatedly, such will often be referred to herein as "long chain alcohol" or UNILIN, but it is to be understood that unless it is clear from the context that the term is to be more restrictive, it is meant to cover the derivatives too.

The fiber-treating and skin-treating materials of the invented compositions, which, together with the suspending agent and stabilizer, are usually the principal active components of the present compositions, are insoluble or marginally soluble in the liquid medium but are emulsifiable, suspendable or dispersible in such medium, due to the presence of the emulsifying agent(s), and the emulsions or suspensions made are stabilized by the long chain alcohol or derivative thereof. The fiber treating and skin-treating materials are usually, but not always those which are desirably substantive to fiber and skin, respectively, as a result of normal uses of the invented compositions. Thus, despite the fact that the concentration of such a treating agent in the composition may be comparatively low and that it may be diluted further, usually with water, before it is applied to a surface to be treated, such material will often be substantive to the treated surface, with a functional proportion thereof remaining on such surface after normal use of the invented composition. In some instances the substantive material will be held to the treated surface despite rinsing off of the composition but in other cases the composition will be applied and allowed to remain on the treated surface, without rinsing or wiping off.

Among the water insoluble treating agents there may be mentioned: petrolatums; paraffin waxes; isoparaffins, mineral oils; microcrystalline waxes; beeswaxes; organosilicon compounds, including silicones and aminosilicones; cationic conditioners, such as quaternary ammonium salts and amines, which can act as antistatic agents; hair conditioners; fiber and fabric softeners; polyethylenes; $C_{18-36}$ triglycerides; higher fatty alcohol esters of higher fatty acids; perfumes; sunscreening compounds; and anti-dandruff agents. Most of the materials listed in this paragraph (and described in more detail below) are conditioning agents for hair, fibrous material or skin which can help to make such feel softer, make skin feel smoother, make hair more controllable and make hair and fabrics static-free. Others of the treating agents can give fibers, hair and skin other desirable properties (anti-dandruff, sunscreening, and perfumed) but still other insoluble substances can be present to impart other characteristics, such as antibacterial and viricidal agents, dyes and pigments, and antioxidants.

Petrolatums are petroleum jellies or mineral jellies which melt in the range of 38° to 60° C. Paraffins (or paraffin waxes) that may be utilized will normally be of chain lengths of 20 to 50 carbon atoms, preferably 20 to 40 carbon atoms, and isoparaffins can be of chain lengths in the range of 12 to 16 carbon atoms, preferably 13 to 15 carbon atoms. Mineral oils (or liquid petrolatums) are liquid and usually are of a density in the range of 0.83 to 0.91 g./ml. at 25° C. The microcrystalline waxes are of an average molecular weight in the range of about 500 to 800 (which is about twice that of the paraffin waxes). Beeswax (yellow) is a complex natural mixture of higher straight chain carboxylic and hydroxycarboxylic acid esters of straight chain $C_{24-36}$ monohydric alcohols of even numbers of carbon atoms. The organosilicon compounds and silicones that may be employed include any of those which are conditioning agents for fibrous materials. Such are normally non-volatile and have been described in parent patent applications Ser. Nos. 07/432,952 now abandoned in favor of Ser. No. 07/806,679, 07/507,328 (now U.S. Pat. No. 4,997,641) and 07/507,335 (now pending), which applications and Ser. Nos. 07/369,361 (now abandoned), 07/369,389 now abandoned in favor of U.S. Pat. No 07/713,478 and 07/432,644 (now U.S. Pat. No. 5,051,250) are hereby incorporated by reference. It has been found that aminosilicones are usually more effective conditioning agents in the compositions of this invention than are conventional silicones, and of such it is preferred to utilize

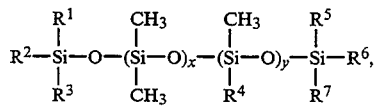

wherein $R^1$, $R^2$, $R^3$, $R^5$, $R^6$ and $R^7$ are alkyls of 1 to 6 carbon atoms, and most preferably of 1 carbon atom each, $R^4$ is $-R^8-NH-CH_2CH_2-NH_2$, $R^8$ is alkylene of 3 to 6 carbon atoms, and most preferably is an isobutyl group, x is an average number in the range of 100 to 10,000, preferably 500 to 10,000, and y is an average number in the range of 1 to 10, most preferably 1, which is of an amine equivalent in the range of 4,000 to 60,000. The amine equivalent of such aminosilicone is preferably in the range of 5,000 to 50,000, more preferably 10,000 to 40,000. Although such aminosilicone is highly preferred, others of the well known group of non-volatile silicones can also be substituted, at least in part, for such aminosilicone.

The cationic conditioning agents are preferably quaternary ammonium salts, although amines and other cationic compounds of fiber conditioning and antistatic properties may also be employed, at least in part. Thus, known amines, amine salts, imidazolinium salts and betaines, and such cationic materials as are described in U.S. Pat. No. 4,000,077 may be substituted for at least some of the quaternary ammonium salt, as may be complexes of cationic and anionic surfactants, such as have been described in U.S. Pat. Nos. 4,896,422 and 4,888,199 and in U.S. patent application Ser. No. 06/916,069 (now U.S. Pat. No. 4,929,367), all of which are incorporated herein by reference.

The preferred quaternary ammonium salts are of the formula $R^9$, $R^{10}$, $R^{11}$, $R^{12}N^+X^-$, wherein at least one of the R groups is lower alkyl and at least one is higher alkyl, with the others being higher and/or lower alkyl. Preferably $R^9$ is lower alkyl, such as of 1 to 4 carbon atoms, $R^{10}$ and $R^{11}$ are higher alkyls of 10 to 40 carbon atoms, $R^{12}$ is such a higher alkyl or lower alkyl, and $X^-$ is a salt-forming anion, such as halide, lower alkosulfate or lower carboxylic acid radical, e.g., chloride, bromide, methosulfate, ethosulfate, citrate or acetate. The lower alkyl will preferably be of 1 to 3 carbon atoms, more preferably being of 1 or 2 carbon atoms, and most preferably, in most cases, will be methyl, and the higher alkyl will preferably be of 10 to 22 carbon atoms, more preferably 12 to 20 carbon atoms, most preferably of 14 to 18 carbon atoms, e.g., 16 to 18 carbon atoms. The anion is preferably a halogen, such as chlorine, bromine or iodine, with chlorine and bromine being preferred and with chlorine being more preferred. It has been found to be desirable to have at least 30 carbon atoms in the quaternary ammonium salt and preferably at least 34. The most preferred higher alkyls are cetyl and stearyl and the most preferred lower alkyl is methyl. The more preferred quaternay ammonium halides include tricetyl methyl ammonium chloride and distearyl dimethyl ammonium chloride, but other quaternary ammonium and amine salts are also operative, including: guar hydroxypropyl trimethylammonium chloride (Cosmedia GUAR-C261, available from Celanese Corp.); polyethylene glycol (PEG 15) coco-polyamine (Polyquat® H81, available from Henkel G.m.b.H.); quaternized hydroxyethyl cellulose, available from Amerchol as Polymers JR and LR; polymers of dimethyldiallyl ammonium chloride or copolymers thereof with acrylamide, available as Merquats 100 and 550; vinyl imidazolevinyl pyrrolidone copolymers, available as Luviquats from BASF Corp.; polyvinyl pyrollidone-dimethylaminoethyl methacrylate copolymers, available as GAFquats from GAF Corp.; dicetyl dimethyl ammonium chloride and tristearyl methyl ammonium chloride and corresponding bromides, amines, amine salts and betaines; and the complexes described in U.S. Pat. Nos. 4,896,422 and 4,888,119 and application Ser. No. 06/916,069 (now U.S. Pat. No. 4,929,367), which are hereby incorporated by reference. Such cationic complexes may also be employed as at least part of the conditioning components of the invented compositions, as was previously mentioned.

The polyethylenes that are utilizable are normally solid powders and, like some other less soluble and less emulsifiable treating agents may be made more soluble and more emulsifiable by the presence of other more soluble and emulsifiable treating agents and other components of the compositions in which they are sometimes dissolved, such as petrolatum. The $C_{18-36}$ triglycerides, which are sold by Croda Corporation, as Syncrowaxes®, such as HGL-C, are triglycerides of such higher molecular weight fatty acids and, like the polyethylenes, in part due to their high molecular weight, are excellent conditioning agents for fabrics, fibers (including human hair) and skin. The higher fatty alcohol esters of the higher fatty acids have been found to be substantive to fibrous materials and skin. Such compounds will normally have carbon atoms contents in the range of 36 to 72 carbon atoms, with the individual alcohols and acids being of 18 to 36 carbon atoms.

Perfumes that are used in the invented composition are usually based on natural and synthetic alcohols, esters, aldehydes, terpenes and musks of known type, with fixatives, and those of the present compositions are preferably perfumes of a type which is normally characterized as long lasting and substantive. Such perfumes are water insoluble and preferably are substantive to and sorbable by proteinaceous substrates, such as hair and skin, but even relatively transient and non-substantive perfumes can be sorbed by the skin and made more effective by being included in the compositions of this invention.

Sunscreening compounds are normally ultraviolet ray absorbing chemicals of known types, among which there may be mentioned the various suitable cinnamates, such as octyl cinnamate and cinoxate, which is 3-(4-methoxyphenyl)-2-propenoic acid 2-ethoxy ethyl ester. Anti-dandruff compounds may include such as zinc pyrithione, sulfur, selenium sulfide and purified coal tar (pixalbol). Of course, the foregoing list is not all-inclusive and various other water insoluble materials for application to and sorption by fibrous materials, including human hair, and human skin, may also be substituted.

The emulsifying agents that are employed in the present invention are surface active materials, including detergents, emulsifiers and hydrotropes. Sometimes emulsification and suspension may be aided by the presence of thickening agents, such as gums, e.g., guar gum, methyl cellulose and hydroxypropyl methyl cellulose, but such materials are not within the scope of the term "emulsifying agents", as employed herein. Rather, they will be considered as thickeners, which are in the group of adjuvants, to be discussed later. Of the detergents and emulsifiers it is preferred to employ those which are anionic but nonionic and amphoteric compounds may also be utilized. Cationic surface active materials are not considered as emulsifying agents because they serve as fiber-treating materials in the invented compositions and are included in such group, although in some cases the cationic conditioning agents also possess emulsifying properties. The anionic detergents and emulsifiers are normally the prime emulsifying agents but any other surfactants present, the long chain alcohol and various adjuvants also may contribute emulsifying properties.

In the preferred anionic surfactants there will be present lipophilic and hydrophilic groups, with the lipophilic group preferably including a higher alkyl chain, such as one of 10 or 20 carbon atoms. The hydrophilic groups of such compounds will normally be salt-forming ions, such as alkali metal, ammonium, lower alkanolamine (mono-, di- and tri-) or magnesium, and such compounds will preferably be sulfates or sulfonates, although phosphonates are also operative. The higher alkyl groups may be in: higher alkyl sulfates; higher alkyl ether sulfates, higher alkyl paraffin sulfonates; higher alkyl aryl sulfonates, such as higher alkylbenzene sulfonates; and/or higher alkylethoxy sulfates (usually of 1 to 6 ethoxy groups per mole, preferably 2 or 3). Additionally, various other anionic surfactants may be employed, including: sulfosuccinates, such as sodium dioctyl sulfosuccinate; sarcosides, such as sodium and lauroyl sarcosides; isethionates, e.g., Igepal ®) A's; and tautares, e.g., Igepon ®) T's.

Although the anionic emulsifiers and detergents are preferred, nonionics are also useful, such as polyethoxylated higher fatty alcohols, polyethoxylated alkyl phenols, condensation products of lower alkylene oxides, and other surface active nonionic compounds which contain satisfactorily balanced hydrophilic and lipophilic groups. Preferably, when they are present the nonionic emulsifiers will be employed as minor components of a system which also includes an anionic surfactant or, if the nonionic is the sole surfactant it will normally be present in less than a detersive proportion. Amphoteric surfactants are also useful and may be employed with the nonionic surfactants or with the anionic surfactants or with mixtures of the two, but usually in such mixtures they too will be minor components. The hydrotropes employed will normally be alkali metal salts of lower alkylbenzene sulfonates wherein the benzene ring may be mono-, di- or tri-substituted, preferably with methyl group(s). Representative of such materials are sodium xylene sulfonate and sodium cumene sulfonate.

Among the preferred surfactant suspending agents are: sodium higher alpha-olefin sulfonate (wherein the olefin is of 12 to 18 carbon atoms, preferably 14 to 16 carbon atoms); sodium lauryl triethoxy sulfate (although 1 to 10 ethoxies may be present); sodium linear higher alkylbenzene sulfonates, such as the dodecyl and tridecylbenzene sulfonates; sodium higher fatty alcohol ethoxy sulfates; sodium ammonium higher alcohol ethoxy sulfates; sodium lauryl sulfate; ammonium higher alkyl sulfates; mono-, di- and tri-lower alkanolamine (1–3 C's) higher fatty alcohol sulfates; nonionic higher fatty alcohol-ethylene oxide condensation products; higher fatty acyl amidopropyl betaines; and lower alkyl substituted aryl sulfonates. Other surfactants and emulsifiers of the types described may be found in various annual editions of McCutcheon's *Detergents and Emulsifiers,* wherein their chemical structures and functions are given.

The fourth component of the present composition is water, although it may contain a minor proportion of polar solvent, such as ethanol, and in some instances, the water may be substantially replaced by such a solvent (although such instances are comparatively rare). The water is preferably deionized so as to have a hardness less than 50 p.p.m., as calcium carbonate. It is also preferred that the water be irradiated to help to prevent any bacterial action.

In addition to the four essential components of the invented compositions, described above, there will also often be present various adjuvants to contribute their particular properties. For example, in liquid detergent compositions one may include magnesium salts, such as magnesium sulfate, and alkanolamides, such as higher fatty acid monoethanolamides and diethanolamides, for their foam improving properties, and may employ higher fatty acid soaps, such as the alkali metal soaps of stearic acid, e.g., sodium stearate, or silicones to control or diminish foaming of synthetic detergents. Cellulose compounds and gums, such as Natrosols ®), Methocels ®), and guar gum may be employed as thickening agents, preservatives and sequestrants may be utilized and the compositions may be colored, perfumed and pH adjusted. The higher alcohol or derivative thereof contributes a pearlescing appearance to the product, the Syncrowax makes it opaque and various of the fiber- and skin-treating materials, such as the waxes, can contribute to the thickening of the product. While soap can diminish foaming of synthetic anionic organic detergents in these compositions, when it is used to replace the detergents it can act as the prime cleaning and foaming agent instead.

Proportions of the various required components of the present compositions will now be given. Such proportions are on the bases of the compositions containing only the required components but normally adjuvants will also be present. Adjuvants' contents can be up to 25% of the compositions but preferably the total of adjuvants will not exceed 15% and often the range will be from 1 to 10% thereof. Of course, when adjuvants are present, the ranges given below will be adjusted accordingly.

The invented liquid fiber- and skin-treating compositions of the invention will comprise 0.3 to 35% of emulsifying agent, 0.3 to 10% of water insoluble treating material, 0.5 to 10% of long chain alcohol and 45 to 98.9% of water. Such ranges cover the various types of the invented treating preparations but because of the diversity of such products more specific ranges will also be given for some such individual types of products.

Hair conditioning shampoos, which are designed to deposit hair conditioning compounds on the hair during the shampooing operation, which compounds remain on the hair despite rinsing, preferably comprise 5 to 25% of emulsifying agent, 0.5 to 5% of water insoluble treating material, 1 to 10% of long chain alcohol and 60 to 93.5% of water. In such compositions the emulsifying agent is preferably lipophile sulfate, selected from the group consisting of higher fatty alcohol sulfates and higher fatty alcohol ethoxylate sulfates, with the ethoxylate sulfates being of 1 to 10 ethoxy groups per mole, and preferably of 2 or 3 ethoxy groups per mole. The lipophiles thereof will normally be higher linear alkyl of 10 to 20 carbon atoms, preferably 10 to 16 carbon atoms and most preferably will be dodecyl. The water insoluble treating material may be any suitable mixture of the compounds described previously under that designation, such as any mixtures of the cationic compounds, waxes, fatty and oily materials previously described and/or present in the working examples. The long chain alcohol will usually be a mixture of long chain alcohols of even numbers of carbon atoms and of normal, bell-shaped distribution curve and such alcohol will average in the range of 28 to 42 carbon atoms. The water will preferably be deionized and irradiated. More preferred embodiments of hair conditioning compositions will comprise 2 to 7% of ammonium or lower (1-3 carbon atoms) mono-, di- or tri-alkanolamine higher fatty alkyl sulfate, wherein the alkyl is preferably of 12 to 15 or 16 carbon atoms, 3 to 8% of alkali metal higher fatty alkyl ethoxylate sulfate (wherein the higher fatty alkyl is preferably of 12 to 16 carbon atoms and the ethoxy content is 1 to 10 moles per mole, more preferably 2 or 3), 0.5 to 5% of higher fatty ester of a lower diol or triol, such as coco fatty acids ester of polyethylene glycol/glycerol, 0.3 to 5% of cationic hair conditioning compound, which is a quaternary ammonium salt and-/or an amine, which have hair conditioning and antistatic properties, 0.5 to 10% of a mixture of long chain alcohols which are of 30 to 40 carbon atoms, and 64 to 93.7% of water.

For anti-dandruff shampoos there will usually be present 5 to 35% of anionic detergent which includes a lipophilic group which is a higher alkyl of 8 to 20 carbon atoms, 0.5 to 10% of a water insoluble anti-dandruff compound, 0.5 to 10% of long chain alcohol and 45 to 94% of water. In preferred anti-dandruff shampoos there will be present 10 to 25% of higher fatty alcohol sulfate, preferably lauryl sulfate, 1 to 4% of anti-dandruff agent, preferably zinc pyrithione, 1 to 10% of the mixture of long chain alcohols of even numbers of carbon atoms in a normal bell-shaped distribution curve, with such chain averaging in the range of 28 to 42 carbon atoms, and 61 to 88.5% of water Instead of employing shampoos for depositing conditioning agents and anti-dandruff chemicals on the hair such deposition may be from hair conditioning compositions, which are primarily for the purpose of applying the conditioning or anti-dandruff compound or other agent onto the hair, and not to clean the hair. Such hair conditioning compositions may comprise 0.3 to 5% of cationic surfactant, 0.5 to 5% of water insoluble hair conditioning material or mixtures of such materials, 0.5 to 10% of long chain alcohol and 80 to 98.7% of water. In preferred embodiments of such aspect of this invention such composition will comprise 0.3 to 1% of a quaternary ammonium salt, such as a higher alkyl tri-lower alkyl ammonium halide, 1 to 10% of a mixture of long chain alcohols averaging 28 to 42 carbon atoms and of a normal distribution, and 87 to 98.2% of water.

Liquid detergent preparations for use in washing the hands and human body comprise 8 to 30% of anionic detergent with a higher alkyl lipophilic group of 8 to 20 carbon atoms, 0.5 to 10% of water insoluble skin conditioning material, 0.5 to 10% of long chain alcohol and 50 to 91% of water. In preferred embodiments of such liquid detergents or "liquid soaps" there are present 10 to 25% of a mixture of higher fatty alcohol ethoxylate sulfate and higher alkyl sulfate detergents in which the higher alkyls are of 12 to 16 carbon atoms and the ethoxylate content of the ethoxylated detergent is 1 to 10 moles per mole, with the ratio of one such detergent to the other being in the range of 1:6 to 6:1, 0.5 to 3% of a mixture of hydrocarbon skin treating agents, preferably mineral oil and petrolatum, or paraffin and microcrystalline waxes, 1 to 5% of water insoluble alcohols, often of even numbers of carbon atoms, of normal distribution and averaging 28 to 42 carbon atoms, and 67 to 88.5% of water.

In addition to compositions that are primarily intended for application to human hair, fibrous materials and/or human skin, some compositions which are intended for other uses can also come into contact with the skin and therefore can be used to condition or treat it. Such preparations include light duty liquid detergents, which may be intended for washing "delicate" fabrics or for dishwashing. These compositions comprise 8 to 35% of anionic detergent which includes a higher alkyl lipophile of 8 to 20 carbon atoms, 0.5 to 5% of water insoluble skin conditioning material, 0.5 to 10% of long chain alcohol and 50 to 91% of water. In preferred embodiments of such compositions there are present 20 to 35% of a mixture of higher alkylbenzene sulfonate and higher fatty alcohol ethoxylate sulfate in a ratio within the range of 1:3 to 4:1, with the alkyl of the alkylbenzene being of 12 to 14 carbon atoms, with the alkyl of the alcohol ethoxylate sulfate being of 12 to 15 carbon atoms and with such compound including 1 to 10 ethoxies per mole, preferably 2 or 3, to 3% of hydrocarbon skin conditioning material, selected from the group consisting of polyethylene, paraffin, petrolatum, mineral oil and microcrystalline wax and mixtures thereof, 0.5 to 3% of beeswax, 1 to 5% of a mixture of long chain alcohols of even numbers of carbon atoms and normal distribution, with such chains averaging in the range of 28 to 42 carbon atoms, and 54 to 78% of water.

Sunscreen preparations which are applied to the human skin are very popular but it is considered that there is also a market for sunscreening hair preparations, including shampoos. Such can be useful for treating dyed hair to prevent bleaching thereof and they may also be employed to apply sunscreens to the skin, including the scalp, thus preventing both sunburn and bleaching of the hair. The suncreen compositions of this invention, which include lotions and shampoos, comprise 1 or 5 to 35% of anionic surfactant which contains a higher alkyl lipophilic group of 8 to 20 carbon atoms, 1 to 5% of water insoluble waxy compound in which the sunscreen compound is soluble, 0.3 to 3% of water insoluble sunscreening compound, 0.5 to 10% of long chain alcohol and 47 to 93.2 or 97.2% of water. In a preferred composition, a shampoo, there are present 10 to 25% of a mixture of anionic detergents which are higher fatty alcohol ethoxylate sulfate and higher alcohol sulfate, with the alcohol being of 12 to 16 carbon atoms, with the ethoxylate content being 1 to 3 moles per mole and with the proportions thereof being in the range of 1:2 to 10:1, 1 to 3% of waxy compounds selected from the group consisting of stearic acid esters and polyethylene, and mixtures thereof, 0.5 to 2% of alkyl lower alkoxy cinnamate sunscreening agent, 1 to 10% of a mixture of long chain alcohols of even numbers of carbon atoms, normal distribution and chains averaging 28 to 42 carbon atoms, and 60 to 87.5% of water.

Although most of the cosmetics, including shampoos are perfumed, and the perfumes are to some extent substantive to surfaces to which they may be applied, so that even after rinsing of such surfaces the fragrance of the perfume is detectable, it is always desirable to improve the strengths of such fragrances on the hair, skin, clothing or fabrics. Therefore, the present invention, wherein the presence of the long chain alcohol promotes greater substantivity of the perfume, as well as improved stability of the composition at elevated temperatures, is of real significance. In a hair perfuming shampoo according to this invention there are present 5 to 35% of anionic detergent which contains a lipophilic group which is a higher alkyl of 8 to 20 carbon atoms, 1 to 5% of water insoluble waxy compound(s), 0.3 to 3% of water insoluble perfume which is sorbable by proteinaceous and other substrates and which is soluble in the waxy compound, 0.5 to 10% of a long chain alcohol and 47 to 93.2% of water. Preferred formulas of this type include 5 to 20% of higher alkyl ethoxylate sulfate wherein the alkyl is of 8 to 20 carbon atoms and the ethoxylate content is 1 to 10 moles per mole, 1 to 5% of higher alkyl sulfate wherein the higher alkyl is of 12 to 16 carbon atoms, 0.5 to 2% of such water insoluble and substantive perfume, 1 to 5% of normal distribution long chain alcohol averaging 28 to 42 carbon atoms per mole, and 68 to 92.5% of water.

The shower gels of this invention comprise about the same components as the liquid emulsions but also should include a sufficient solids content to promote gel formation, and sometimes will also include synthetic or natural gums to assist gelation, too. Thus, they can include 5.0 to 35% of emulsifying agent, 0.3 to 10% of treating materials, 0.5 to 10% of long chain alcohol and 40 to 94.2% of water, with 0.0 or 0.5 to 5% of gum and at least enough solids content to promote gelation at room temperature (usually at least 20%).

The following examples are given to illustrate specific working embodiments of the invention but are not to be interpreted as limitative thereof. Unless otherwise indicated all parts and percentages in these examples, this specification and the appended claims are by weight and all temperatures are in °C.

EXAMPLES 1–4

| Component | Percent (by weight) Examples No's. | | | |
|---|---|---|---|---|
| | 1 | 2 | 3 | 4 |
| (1) PVP K-30 | 0.30 | — | — | — |
| Honey | 0.50 | — | — | — |
| PEG 7 Glyceryl cocate | 2.00 | — | 0.50 | — |
| (2) Cosmedia Guar C261 | 1.20 | 0.75 | — | 1.00 |
| Sodium lauryl diethoxy sulfate | 5.60 | 6.00 | 6.00 | 6.00 |
| Monoethanolamine lauryl sulfate | 5.00 | 6.00 | 6.00 | 6.00 |
| (3) PEG 15 coco polyamine | 0.50 | 0.50 | 0.50 | 0.50 |
| (4) Dehydol L-53 | 1.00 | 1.00 | — | — |
| (5) Euperlan PK-771 | 3.00 | 3.00 | 3.00 | 3.00 |
| Perfume | 0.80 | 0.80 | 0.80 | 0.80 |
| (6) UNILIN 425 | 3.00 | 3.00 | 3.00 | 3.00 |
| (7) Microcrystalline wax | — | 1.00 | 1.00 | — |
| (8) Petrolatum | — | 1.00 | — | — |
| (9) Paraffin wax | — | — | 1.00 | |
| (10) Polymer Jr-30M | — | — | 0.60 | 0.50 |
| Monobasic ammonium phosphate | — | — | 0.30 | 0.30 |
| Water, deionized, irradiated | 77.10 | 76.95 | 77.30 | 78.90 |
| | 100.00 | 100.00 | 100.00 | 100.00 |

(1) Polyvinyl pyrrolidone, mfd. by BASF Corp.
(2) Guar hydroxypropyl trimethylammonium chloride
(3) Polyquat H81
(4) $C_{12-14}$ fatty alcohols triethoxy sulfate, mf'd. by Henkel
(5) Mixture of sodium laurethoxy sulfate, glycol distearate and coco monoethanolamide, mf'd. by Henkel
(6) 80–85% of saturated primary linear polymeric alcohols of $C_{18-44}$ normal carbon atoms distribution, with 15–20% of corresponding hydrocarbons, of average molecular weight of about 425.
(7) MP = 82° C.
(8) Contain 60% n-alkanes averaging 27–33 carbon atoms, with a distribution curve peak in that range.
(9) $C_{20-40}$ straight chain paraffins, MP = 36° C.
(10) Quaternized hydroxyethyl cellulose The above four formulas of conditioning shampoos which contain polycationic hair treatment agents together with emulsion stabilizing higher alcohol (UNILIN 425) are made by mixing together the water, surfactants and water soluble components, with appropriate heating to about 70°–80° C., melting the lipophilic components, except for perfume, together at a similar temperature, mixing the two mixes together, cooling, and admixing in the perfume. The products resulting are stable conditioning shampoos in pearlescent liquid emulsion form, which are of viscosities in the range of 2,000 to 6,000 centipoises at 25° C., depending on the formulas, and which are stable against phase separations during and after one month's storage at elevated temperature (49° C.). Control compositions from which the UNILIN 425 is omitted separate into different phases after less than one week's storage at such temperature. In normal storage, even in warehouses in southern states, it is considered that such shampoos will not normally be subjected to more severe storage conditions than one month at 49° C., so the invented compositions are sufficiently stable (and often they will be stable for three months or more of storage at 49° C.). Thus, the invented compositions are suitable for commercial production and warehouse storage for products to be nationally marketed, but the control compositions do not pass such test.

The conditioning shampoos made leave the hair desirably conditioned (easier wet combing and dry combing and less static and fly-away action) after shampooing and the presence of the UNILIN 425 promotes deposition of the contained hair conditioning agents on the hair during shampooing and promotes retention of such agents on the hair despite rinsing, leading to conditioning superiority over control compositions which do not contain UNILIN 425.

Various other waxy and lipophilic conditioning agents may be substituted for those of the described formulas and other UNILIN's, such as UNILIN 550 may be used in replacement of UNILIN 425 and similar results will be obtained. UNILIN's 325, 350 and 700 may replace the other UNILIN's mentioned in part, with UNILIN 425 and/or UNILIN 550 still being present in major proportion(s), and in some instances mixtures of UNILIN's 325 and 700 or 350 and 700 may be utilized, preferably with a major proportion of the total UNILIN's content of the resulting shampoos being of UNILIN's 425 and/or 550. Sometimes, as when the compositions are of borderline stability or are not very unstable without the UNILIN present, UNILIN's 325 and 350 may be used alone and can be effective stabilizers, sometimes in increased proportions compared to the proportions of UNILIN's 425 and 550 that would be stabilizing.

EXAMPLE 5

| Component | Percent (by weight) |
|---|---|
| Sodium linear dodecylbenzene sulfonate | 17.0 |
| Sodium lauryl alcohol triethoxy sulfate | 13.0 |
| Lauric myristic monoethanolamide | 4.0 |
| (11) Hydrotrope mixture | 3.0 |
| Magnesium sulfate (anhydrous) | 1.0 |
| Beeswax, yellow | 1.0 |
| (8) Petrolatum | 1.0 |
| Perfume | 0.3 |
| Colorant (dye mixture) | 0.1 |
| Ethyl alcohol (95%) | 5.0 |
| (6) UNILIN 425 | 3.0 |
| Deionized water (irradiated) | 51.6 |
| | 100.0 |

(11) Approximately equal mixture of sodium cumene sulfonate and sodium xylene sulfonate The light duty liquid detergent of this example is made by essentially the same method as that of Examples 1–4, with the perfume, colorant and ethyl alcohol being added to the cooled hydrophile-lipophile mixture. The result is a stable pearlescent liquid detergent in emulsion form, which is stable on storage when subjected to the elevated temperature storage test, as recited in Examples 1–4. The liquid detergent is an excellent mild detergent which satisfactorily cleans fabrics, as well as dishes, and leaves the hands softer and smoother than do control compositions which do not contain the UNILIN 425. Furthermore, such control compositions are not usually satisfactorily stable at elevated temperatures.

The skin conditioning effect of the described light duty liquid detergent composition is attributable to the presence of the UNILIN 425, which, in addition to stablilizing the emulsion, aids deposition of the skin conditioning agents, beeswax and petrolatum, onto the skin and additionally improves the retention of such agents on the skin despite rinsing.

EXAMPLES 6–9

| | Percent (by weight) Examples No's. | | | |
|---|---|---|---|---|
| Component | 6 | 7 | 8 | 9 |
| Ammonium lauryl triethoxy sulfate | 14.0 | 7.0 | 3.0 | 3.0 |
| Glycerine | 2.0 | 2.0 | 1.0 | 1.0 |
| Coco diethanolamide | 5.0 | 5.0 | 5.0 | 5.0 |
| Perfume | 1.0 | 1.0 | 1.0 | 1.0 |
| (12) Germaben II | 0.5 | 0.5 | 0.5 | 0.5 |
| Colorant (dye mixture) | 0.1 | 0.1 | 0.1 | 0.1 |
| (13) Britol 50 | 0.5 | — | 0.5 | — |
| (8) Petrolatum | 0.5 | — | 0.5 | — |
| (6) UNILIN 425 | 3.0 | 3.0 | 3.0 | 3.0 |
| Sodium chloride | 0.3 | 0.3 | 0.3 | 0.3 |
| Ammonium lauryl sulfate | — | 7.0 | 3.0 | 3.0 |
| Sodium alpha $C_{14-16}$ olefin sulfonate | — | — | 10.0 | 10.0 |
| (9) Paraffin wax | — | 0.5 | — | 0.5 |
| (7) Microcrystalline wax | — | 0.5 | — | 0.5 |
| (14) Coco amidopropyl betaine | — | 2.0 | 2.0 | 2.0 |
| Deionized water | 73.1 | 71.1 | 70.1 | 70.1 |
| | 100.0 | 100.0 | 100.0 | 100.0 |

(12) Preservative (Sutton Laboratories, Inc.)
(13) Mineral Oil, of molecular weight in the range of 400 to 800 (available from Witco/Penreco Corp.)
(14) Tego-betaine L-7 (available from Goldschmidt Chemical Co.)

The shower gels of Examples 6 and 7 and the "liquid soaps" (really liquid detergent preparations) of Examples 8 and 9 are made by the procedures previously described, except that for the shower gels the perfume, colorant and preservative are mixed with the mix of hydrophilic and lipophilic components after partial cooling and before gelation. The shower gels are in solid gel form and the liquid soaps are in readily pumpable liquid state with the difference in physical states being largely attributable to the different surfactants utilized. The compositions of these examples all leave the skin feeling softer and smoother, with less objectionable "dryness" than control products that do not contain the UNILIN component. Also, the liquid soap does not separate into different phases at elevated temperatures but maintains its uniformity throughout dispensing from a pump-type dispenser, while control products that do not contain the long chain alcohol tend to separate at elevated temperatures.

Various changes can be made in the given formulations and the same desired results will be obtained. For example, ammonium lauryl triethoxy sulfate and ammonium lauryl sulfate may be replaced by the corresponding sodium salts. UNILIN 425 may be replaced by UNILIN 550 and other mixtures of some or all of the paraffin wax, microcrystalline wax, mineral oil and petrolatum may be employed and other known hydrocarbyl and other skin treating agents, such as polyethylenes, may also be utilized, with stable and effective conditioner-depositing (on the skin) compositions being obtained. When the UNILIN 425 is omitted from the various formulas the "liquid soaps" are noticeably less stable on storage and tend to separate at elevated temperatures, and the skin conditioning components of the compositions are less effective, apparently being less substantive to the skin in the absence of the UNILIN.

EXAMPLE 10

| Component | Percent (by weight) |
|---|---|
| Ammonium lauryl sulfate | 15.0 |
| Coco diethanolamide | 4.0 |
| Zinc pyrithione | 2.0 |
| (6) UNILIN 425 | 3.0 |
| Perfume | 0.7 |
| (12) Germaben II | 0.5 |
| Color (dye and/or pigment mixture) | 0.1 |
| Water | 74.7 |
| | 100.0 |

The anti-dandruff shampoo of this invention is made by the procedure previously described with respect to liquids of Examples 1–9. The result is a stable and effective anti-dandruff shampoo of desired viscosity (desirable viscosities are in the 1,000–10,000 centipoises range) of about 2,000 centipoises at 25° C. which is stable under elevated temperature storage of one month at 49° C., and which satisfactorily deposits (and retains) its anti-dandruff component (zinc pyrithione) on the scalp after shampooing and rinsing. Control shampoos that do not contain the UNILIN 425 (or other equivalent UNILIN or long chain alcohol, of types previously described in these examples and in the specification), are not satisfactorily phase stable on elevated temperature storage and do not deposit the zinc pyrithione on the scalp to the same effective extent. Similar effective depositions of other water insoluble anti-dandruff agents (such as climbazole and piroctone olamine) are also obtainable by substituting them for the zinc pyrithione or by substituting mixtures of two or more of such compounds for the zinc pyrithione.

EXAMPLE 11

| Component | Percent (by weight) |
|---|---|
| (15) Cetrimonium chloride | 0.5 |
| (6) UNILIN 425 | 3.0 |
| (13) Britol 50 | 1.0 |
| (12) Germaben II | 0.5 |
| Water, deionized and irradiated | 95.0 |
| | 100.0 |

(15) Cetyl trimethyl ammonium chloride

This hair conditioning rinse or lotion is made in the manner previously described, with the cetrimonium chloride serving as the surfactant and emulsifying agent. The emulsion resulting is stable at elevated temperatures and the UNILIN 425 aids in depositing and retaining the cetrimonium chloride and Britol 50 on the hair so as better to condition it. The control, without UNILIN 425 in the emulsion, is unstable at 49° C., and hair treated with it is not conditioned as well as when it is treated with the invented composition.

EXAMPLES 12–14

| | Percent (by weight) Examples No's. | | |
|---|---|---|---|
| Component | 12 | 13 | 14 |
| (16) Distearyl dimonium chloride | 6.0 | 6.0 | 2.0 |
| (17) Amine citrate complex | — | — | 6.0 |
| Beeswax, yellow | — | 0.5 | 0.8 |
| (8) Petrolatum | 0.5 | 0.5 | — |
| Sodium citrate | 0.1 | 0.1 | 0.1 |
| Propylene glycol | 0.1 | 0.1 | 0.1 |
| (6) UNILIN 425 | 3.0 | 3.0 | 3.0 |
| Water, deionized | 90.3 | 89.8 | 88.0 |
| | 100.0 | 100.0 | 100.0 |

(16) distearyl dimethyl ammonium chloride
(17) Complex of citric acid and suitable amine, such as distearyl methyl amine, which complex has cationic properties like those of quaternary ammonium salts employed in other examples The fabric softeners of these examples are manufactured in the manner previously described and produce stable pearlescent emulsions which do not separate out after one month's storage at 49° C. The products made are effective fabric softeners, with the quaternary ammonium salt, the amine citrate complex (which is in the nature of a quaternary ammonium salt) and the petrolatum serving to soften and condition fabrics treated with the compositions, even after rinsing thereof. Control compositions which do not contain the UNILIN 425 (or other equivalent UNILINs) fail the elevated temperature stability test and are not as effective in conditioning fabrics and fibers, which is considered to be due to the fact that the conditioning agents are not as substantive to the fibers in the wash water when the long chain alcohol or derivative thereof is absent.

| | Percent (by weight) Examples No's. | | | | | | | |
|---|---|---|---|---|---|---|---|---|
| Component | 15 | 16 | 17 | 18 | 19 | 20 | 21 | 22 |
| Sodium alpha $C_{14-16}$ olefin sulfonate | 14.00 | 14.00 | 10.00 | 5.00 | 7.00 | 15.00 | — | — |
| Coco amidopropyl betaine | 3.00 | 3.00 | 2.50 | 1.00 | 3.00 | 4.00 | 2.00 | — |
| Sodium lauryl triethoxy sulfate | 1.00 | 1.00 | 3.00 | 10.00 | 5.00 | — | 15.00 | 15.00 |
| (18) Coco diethanolamide | 2.00 | 3.00 | 1.00 | 5.00 | 0.50 | 4.00 | 3.00 | 3.00 |
| Hydroxyethyl cellulose | 0.50 | 0.30 | 1.00 | — | — | 0.75 | 0.75 | 0.52 |
| (19) AC Polyethylene 617-A | 1.00 | 0.50 | — | — | — | — | — | — |
| (13) Britol 50 | 1.00 | 1.50 | — | — | — | — | — | — |
| Beeswax, yellow | 1.00 | 2.00 | 3.00 | 4.00 | — | — | — | — |
| (6) UNILIN 425 | 2.00 | 2.00 | 2.00 | 2.00 | 2.00 | 2.00 | 2.00 | 2.00 |
| (8) Petrolatum | — | — | 0.75 | 1.50 | 3.00 | — | — | — |
| (20) Silicone | — | — | — | — | — | 0.75 | 2.00 | 3.00 |
| Tri ($C_{18-22}$ alkyl) methyl ammonium chloride | 0.50 | 1.00 | — | — | — | 0.25 | 0.20 | — |
| Ethylene glycol distearate | — | 1.50 | 1.00 | 1.25 | 0.75 | 0.50 | — | — |
| (12) Germaben II | 0.50 | 0.50 | 0.50 | 0.50 | 0.50 | 0.50 | 0.50 | 0.50 |
| Colorant (dye mixture) | 0.10 | 0.10 | 0.10 | 0.10 | 0.10 | 0.10 | 0.10 | 0.10 |
| Perfume | 1.00 | 1.00 | 1.00 | 1.00 | 1.00 | 1.00 | 1.00 | 1.00 |
| Water, deionized and irradiated | 71.40 | 68.60 | 74.15 | 68.40 | 76.90 | 71.15 | 73.20 | 74.88 |

-continued

| | Percent (by weight) Examples No's. | | | | | | | |
|---|---|---|---|---|---|---|---|---|
| Component | 15 | 16 | 17 | 18 | 19 | 20 | 21 | 22 |
| | 100.00 | 100.00 | 100.00 | 100.00 | 100.00 | 100.00 | 100.00 | 100.00 |

(18) Natrosols, e.g., 250 HR and 300 PA, (Hercules Corp.)
(19) Polyethylene homopolymers of molecular weight in the range of 2,000 to 4,000 (Allied Signal Corp.)
(20) Silicone X2-8107-Type 2 (Dow Corning Corp.), which is an amino-silicone of an amine equivalent of 4,000 or more, (described in our U.S. Pat. application S.N. 07/432,952)

The liquid soaps of Examples Nos. 18 and 19 are made in the manner described in the previous examples and, like the liquid compositions of those examples, are stable against separation at elevated temperatures and are of improved skin smoothening and softening properties, compared to control compositions which do not include the UNILIN 425 or other such long chain alcohols. The shower gel preparations of Examples 15-17 HGL-C instead of UNILIN 425 will be as stable as the UNILIN-containing liquid soaps under elevated temperature conditions nor should they be expected to make water insoluble treating agents of the compositions as effectively substantive to substrates as does the UNILIN. Additionally, the Syncrowaxes tend to make the product opaque, instead of pearlescent, which may not be as desirable an effect.

| | | Percent (by weight) Examples No's. | | | | | | | |
|---|---|---|---|---|---|---|---|---|---|
| | Component | 23 | 24 | 25 | 26 | 27 | 28 | 29 | 30 |
| | Ammonium lauryl sulfate | 12.50 | 10.00 | 8.00 | 6.00 | 4.00 | 12.50 | 12.50 | 12.50 |
| | Sodium lauryl ethoxy sulfate | 2.50 | 5.00 | 2.50 | 9.00 | 5.00 | 2.50 | 2.50 | 2.50 |
| | Ammonium decyl diethoxy sulfate | — | — | 4.50 | — | 6.00 | — | — | — |
| | Coco diethanolamide | 3.50 | 2.00 | 3.00 | — | — | — | — | — |
| | Lauric diethanolamide | — | — | — | 3.50 | 3.00 | 2.50 | 2.00 | 3.50 |
| (18) | Hydroxyethyl cellulose | 0.25 | 0.40 | 0.50 | 0.90 | 1.20 | 0.65 | 0.75 | — |
| (19) | AC Polyethylene 617A | 1.00 | 1.50 | 2.00 | 0.50 | 0.35 | 0.75 | — | — |
| (13) | Britol 50 | 0.75 | 1.50 | 1.50 | 0.75 | 0.25 | 0.25 | 1.00 | 1.25 |
| | Beeswax, yellow | — | 0.25 | 0.50 | 3.00 | 4.00 | 0.50 | 6.00 | — |
| (20) | Syncrowax HGL-C | 0.75 | 0.25 | 1.50 | 2.50 | — | — | — | — |
| (6) | UNILIN 425 | 1.00 | 1.50 | 0.50 | 0.75 | 1.00 | 1.00 | 1.00 | 1.00 |
| (8) | Petrolatum | 0.25 | 0.50 | 0.75 | 1.00 | 2.00 | — | — | 4.00 |
| (9) | Paraffin wax | 0.25 | 0.50 | 1.00 | 2.00 | — | — | 3.00 | — |
| (7) | Microcrystalline wax | 1.00 | — | — | — | 2.00 | — | — | — |
| | Dimethicone | — | — | — | — | — | 2.00 | — | — |
| | Trilauryl methyl ammonium chloride | 1.00 | 2.50 | 0.50 | 0.25 | — | 2.00 | — | 1.50 |
| | Ethylene glycol distearate | — | — | — | — | 1.00 | 1.50 | 1.25 | 0.75 |
| (12) | Germaben II | 0.50 | 0.50 | 0.50 | 0.50 | 0.50 | 0.50 | 0.50 | 0.50 |
| | Colorant (dye mix) | 0.10 | 0.10 | 0.10 | 0.10 | 0.10 | 0.10 | 0.10 | 0.10 |
| | Perfume | 1.00 | 1.00 | 1.00 | 1.00 | 1.00 | 1.00 | 1.00 | 1.00 |
| | Water, deionized | 73.65 | 72.50 | 71.65 | 68.25 | 68.60 | 72.25 | 68.40 | 71.40 |
| | | 100.00 | 100.00 | 100.00 | 100.00 | 100.00 | 100.00 | 100.00 | 100.00 | and 20-22 are made in the manner described with respect to the gels of Examples 6 and 7 and are also of improved skin treating properties, compared to controls which do not contain the higher alcohol component. Various formulas given in the above Examples 15-22 may be modified, as by increasing the water content and decreasing the hydroxyethyl cellulose content, to convert gels to liquids, or by reversing such changes, as a result of which the liquid preparations may be converted to gel form.

In other variations of these examples hydroxyethyl cellulose may be replaced by methyl cellulose, hydroxypropyl methyl cellulose, and suitable natural gums, such as guar gum, the polyethylene may be replaced by other polyethylenes, such as AC Polyethylenes 7A, 8A and 9A, or mixtures thereof, the silicone may be replaced by dimethicone or other suitable silicones and aminosilicones, described in previously mentioned U.S. patent application Ser. No. 07/432,952, and the quaternary ammonium salt may be replaced by other quaternary ammonium salts, such as di-($C_{18-22}$ alkyl) dimethyl ammonium chloride. Also, the anionic detergents may be employed in their sodium, ammonium and triethanolamine salt forms and in some cases the long chain alcohol content may be at least partially replaced by Syncrowax HGL-C. However, it should not be expected that liquid soap compositions containing Syncrowax The hair conditioning shampoos of Examples 23-30 are made in the manner previously described with respect to Examples 1-5, 8-14, 18 and 19 and the resulting shampoos are stable and do not separate on storage for one month at elevated temperatures. They are superior to control shampoos that do not contain the higher fatty alcohol component (UNILIN 425) in both stability and in promoting deposition on the hair and retention by it of hair conditioning components of the shampoo during shampooing, and despite rinsing. Thus, the invented shampoos of these examples are better conditioning shampoos than are controls from which the UNILIN 425 and other higher alcohols of this type have been omitted.

Variations of the described hair conditioning shampoos are made in which ammonium lauryl sulfate is replaced by sodium and/or triethanolamine lauryl sulfate(s), ammonium decyl diethoxy sulfate is replaced by the corresponding sodium and/or triethanolamine decyl diethoxy sulfate(s), hydroxyethyl cellulose is replaced by methyl cellulose, hydroxypropyl methyl cellulose and/or guar gum, the polyethylene is replaced by AC Polyethylenes 7A, 8A or 9A and/or mixtures thereof, the UNILIN 425 is replaced by UNILIN 550, mixtures of UNILIN 425 and 550 or mixtures of UNI- LIN 325, 350 and 770 with UNILIN 425, and the tri-higher alkyl mono-lower alkyl ammonium halide is replaced by di-higher alkyl di-lower alkyl ammonium halide, e.g., dilauryl dimethyl ammonium chloride. The shampoos resulting are also of improved phase stability on elevated temperature storage and of improved hair conditioning power, compared to a UNILIN-free control.

EXAMPLE 31

| Component | Percent (by weight) |
| --- | --- |
| Ammonium lauryl diethoxy sulfate | 7.50 |
| Ammonium lauryl sulfate | 7.50 |
| Coco diethanolamide | 3.50 |
| (6) UNILIN 425 | 3.00 |
| (19) AC Polyethylene 617-A | 0.75 |
| (13) Britol 50 | 1.00 |
| (21) Climbazole | 0.75 |
| Perfume | 0.70 |
| (12) Germaben II | 0.50 |
| Sodium chloride | 0.30 |
| Colorant (dye mixture) | 0.10 |
| Deionized water | 74.40 |
|  | 100.00 |

(21) Anti-dandruff agent, mfd. by Bayer, A.G.

An anti-dandruff shampoo of the above formula is made by the procedures previously described for other shampoos and liquid detergent compositions. The result is a phase-stable (at elevated temperatures) shampoo from which the climbazole is depositable upon the scalp after shampooing, of which an effective amount thereof is retained even after subsequent rinsing. An anti-dandruff amount of the climbazole adheres to the hair and remains on it, in part due to the action of the UNILIN 425, to produce a significant anti-dandruff effect, which is superior to that obtainable from a control formula from which the UNILIN 425 is omitted. The Britol 50 also helps to promote emulsification of the climbazole and aids in producing a uniform emulsion, from which the climbazole is deposited uniformly on the scalp during use. In variations of the formula other anti-dandruff compounds may be substituted in whole or in part for the climbazole, such as zinc pyrithione and/or piroctone olamine, and the same improved elevated temperature stability and anti-dandruff actions, compared to controls from which the UNILIN 425 was omitted, are obtainable.

EXAMPLES 32 & 33

| | | Percent (by weight) Examples No's. | |
| --- | --- | --- | --- |
| | Component | 32 | 33 |
| | Ammonium lauryl diethoxylate sulfate | 12.50 | 7.50 |
| | Ammonium lauryl sulfate | 2.50 | 7.50 |
| | Lauric monoethanolamide | 3.50 | — |
| | Coco diethanolamide | — | 3.50 |
| | Ethylene glycol distearate | 0.75 | — |
| | Stearyl stearate | 0.35 | — |
| (6) | UNILIN 425 | 2.00 | 3.00 |
| (19) | AC Polyethylene 617-A | 0.75 | 0.75 |
| (22) | Parsol MCX | 1.00 | 1.00 |
| | Tricetylmethylammonium chloride | 0.50 | — |
| | Perfume | 0.75 | 0.70 |
| (12) | Germaben II | 0.50 | 0.50 |
| | NaCl | 0.30 | 0.30 |
| | Deionized water | 74.60 | 75.25 |

-continued

| | | Percent (by weight) Examples No's. | |
| --- | --- | --- | --- |
| | Component | 32 | 33 |
| | | 100.00 | 100.00 |

(22) Octyl methoxycinnamate

The sunscreening shampoos of Examples 32 and 33 are made according to the procedure previously described in these examples for manufacturing the liquid emulsions thereof and are stable against separation at elevated temperatures, up to 49° C. for one month, and the sunscreen component thereof (octyl methoxycinnamate) is substantive to skin and hair from such compositions, with such stability and substantivity being better than for control compositions from which the UNILIN 425 has been omitted. In variations of the formulas the octyl methoxycinnamate is replaced by other sunscreening agents, such as other middle and higher alkyl lower alkoxy cinnamates, cinoxate and other sunscreening compounds previously mentioned in this specification, and equivalent results are obtainable. Under ultraviolet light the actual deposition of the sunscreen on the hair and on the scalp can be identified, as well as build-up of the concentration thereof (or at least maintenance of such concentration) by repeated shampooings of the hair with such compositions.

EXAMPLE 34

| Component | Percent (by weight) |
| --- | --- |
| Ammonium lauryl diethoxylate sulfate | 12.50 |
| Ammonium lauryl sulfate | 2.50 |
| Coco diethanolamide | 3.50 |
| (6) UNILIN 425 | 3.00 |
| (19) AC Polyethylene 617-A | 0.75 |
| (13) Britol 50 | 1.00 |
| Fragrance | 1.00 |
| (12) Germaben II | 0.50 |
| Sodium chloride | 0.30 |
| Colorant (dye mixture) | 0.10 |
| Deionized water | 74.85 |
|  | 100.00 |

The hair fragrance depositing shampoo of this invention is made in the same manner as was previously described in the examples relating to other liquid emulsions except for the fact that the fragrance (a substantive perfume) is incorporated in the lipophilic pre-mix at 85° C. (and therefore it should be heat stable), instead of being added to the mixed and cooled lipophilic and hydrophilic pre-mix. The product resulting is a satisfactory shampoo, which cleans the hair efficiently and leaves on it a noticeably detectable increased amount of fragrance, compared to a control formula from which the UNILIN 425 has been omitted, and it also conditions the hair better, due to the presence of the UNILIN. Thus, as in others of the working examples, the UNILIN 425 and other such long chain alcohols promote desired depositions on the hair of certain lipophilic components of these stable emulsions described, in addition to improving heat stability of such liquid emulsions. By appropriate modifications of formulations (to include other active components) one can also deposit lipophilic colorants, such as dyes, lipophilic microbicides and other lipophilic materials for treating hair, skin and fibrous materials.

EXAMPLE 35

The proportions of various components may be modified ±10, ±20 and ±30% from those given in the preceding working examples and satisfactory and operative products will be obtained, providing that the resulting proportions are not outside the ranges previously mentioned in the specification.

In the foregoing working examples the substances to be deposited on hair, skin or fibrous materials may be varied, with a main consideration being that they should be substantially or completely water insoluble but emulsifiable in the presence of the emulsifying system and higher alcohol of the type described. Often it will be desirable to employ other lipophiles, such as liquid hydrocarbons, to assist in the emulsification of the water insoluble treating agent but in most cases that is not necessary. Manufacturing methods may be modified and adapted to particular formulations and components thereof but in general all the lipophilic materials should be in liquid form when the emulsion is being created, which is normally at elevated temperature, and heat sensitive components should normally be added to the emulsion after it has been cooled to approximately room temperature.

Although most of the products of this invention are in liquid emulsion form they may also be produced in solid or gel form, as been previously described. Thus, shower gels may be made by utilizing thickening additives, such as synthetic or natural gums, and by varying the proportions of components of the composition to increase the solids content thereof. Of course, when the invented compositions are in gel form, elevated temperature stability and phase separation are not of as much significance as they are for liquid emulsions but the adherence-promoting characteristics of the invented compositions still make them advantageous, compared to controls that do not contain the long chain alcohols or their derivatives of this invention. Among such derivatives that can be useful are the long chain fatty acids, the long chain fatty acid esters of the UNILIN alcohols and the corresponding ethylene oxide derivatives of such alcohols, such as Unithoxes (also available from Petrolite Corp.)

The liquid emulsions of the invention normally will be of a viscosity in the range of 1,000 to 10,000 centipoises at 25° C., preferably 2,000 to 6,000 cps. and often more preferably 2,000 to 4,000 cps. The pH's of the compositions may vary but will normally be in the range of 4 to 9, preferably 5 to 8, e.g., 6 or 7. Emulsions made will be pearlescent in appearance and sometimes may appear opaque, due to the presence of the desired higher alcohol (UNILIN) in the compositions. Similarly, the solid and gel products will be pearlescent and sometimes opaque in appearance, too. In some instances Syncrowaxes may be substituted, at least in part, for the long chain ($C_{26-43}$ average) alcohols but when complete substitution is effected desirable emulsion stabilization and adherence characteristics of the product are often adversely affected.

The invention has been described with respect to working examples and illustrations thereof but is not to be limited to these because it is evident that one of skill in the art, with the present specification before him/her, will be able to utilize substitutes and equivalents without departing from the invention.

What is claimed is:

1. A hair treating composition which is a stable aqueous emulsion, suspension or dispersion of a water insoluble hair treating material, said material being selected from the group consisting of beeswax, petrolatum, paraffin wax, isoparaffin, mineral oil, microcrystalline wax, silicone, perfume, quaternary ammonium salt, amine antistatic agent, polyethylene, $C_{18-36}$ triglyceride, higher fatty alcohol ester of higher fatty acid, and sunscreening compound, and mixtures thereof, said composition comprising 0.3–10% of said water insoluble hair treating material, 0.3–35% of anionic surface active agent, and 0.5–10% of a stabilizing agent for the composition, said stabilizing agent being selected from the group consisting of long chain primary alcohols, of a weighted average number of carbon atones in the range of 26 to 43, alkoxylated such alcohols fatty acids of a weighted average number of carbon atoms in the range of 26 to 43 and primary lower alcohol esters of said fatty acids in which the alcohol is of 1 to 4 carbon atoms, and mixtures thereof.

2. A hair conditioning shampoo according to claim 1 which comprises 2 to 8% of ammonium or lower alkanolamine higher fatty alkyl sulfate, wherein the lower alkanolamine is of 1 to 3 carbon atoms and the higher fatty alkyl is of 12 to 16 carbon atom; 2 to 8% of alkali metal higher fatty alkyl ethoxylate sulfate wherein the alkyl is of 12 to 16 carbon atoms; 0.5 to 5% of $C_{18-36}$ triglyceride insoluble hair treating material; 0.3 to 5% of quaternary salt; 1 to 10% of said mixture of long chain alcohols; and 65 to 93.2% of water.

3. A hair treating composition according to claim 1 which is stable at a temperature of 43° C., wherein said stabilizing agent is a long chain alcohol of a weighted number of carbon atoms in the range of 30 to 40.

4. A hair treating composition according to claim 1 which is selected from the group consisting of shampoos, perfuming shampoos, hair conditioning compositions, hair setting compositions, antidandruff shampoos, antistatic compositions and sunscreens.

5. An anti-dandruff shampoo according to claim 4 which comprises 10 to 25% of said anionic surface active agent, which is a higher fatty alcohol sulfate wherein the alcohol is of 8 to 20 carbon atoms, 1 to 4% of said water insoluble hair treating material, which is zinc pyrithione, 1 to 10% of said insoluble long chain alcohol, which is a mixture of long chain alcohols of even numbers of carbon atoms and normal distribution, with such chains averaging in the range of 28 to 42 carbon atoms, and 61 to 88% of water.

6. A composition according to claim 4 which is a hair perfuming shampoo which comprises 5 to 35% of said anionic surface active agent, which is an anionic detergent which contains a higher alkyl of 8 to 20 carbon atoms, 1 to 5% of a first said hair treating material, which is a water insoluble wax, 0.3 to 3% of a second said hair treating material, which is a water insoluble perfume which is at least partially sorbable by proteinaceous substrates and which is soluble in the wax, 0.5 to 5% of said long chain alcohol, and said aqueous medium, which includes 47 to 93.2%, on a composition basis, of water.

7. A composition according to claim 4 which comprises 45 to 98.9% of water.

8. A composition according to claim 4 in the form of an anti-dandruff shampoo wherein said water insoluble hair treating material is an anti-dandruff compound.

9. A hair treating composition according to claim 7 wherein the distribution of the carbon chains in the long chain alcohol substantially follows a normal distribution curve.

10. A composition according to claim 9 wherein said long chain alcohol is of a weighted average chain of about 30 carbon atoms.

11. A composition according to claim 10 wherein there is present with the long chain alcohol a mixture of hydrocarbon substantially corresponding in chain lengths with the alcohols, and in total amount which is less than ½ of such alcohol content.

12. A composition according to claim 7 which is a hair conditioning shampoo in which the anionic surface active agent comprises 5 to 20% of a lipophile sulfate in which the lipophile group includes an alkyl of 10 to 20 carbon atoms, 0.5 to 5% of the water insoluble hair treating material, 1 to 10% of a mixture of said long chain alcohols of even numbers of carbon atoms and normal distribution, with such chains averaging in the range of 20 to 42 carbon atoms, and 65 to 93.5% of water.

* * * * *